Jan. 10, 1950 C. HARTGERINK Plant Pat. 912
ROSE PLANT
Filed Oct. 27, 1948
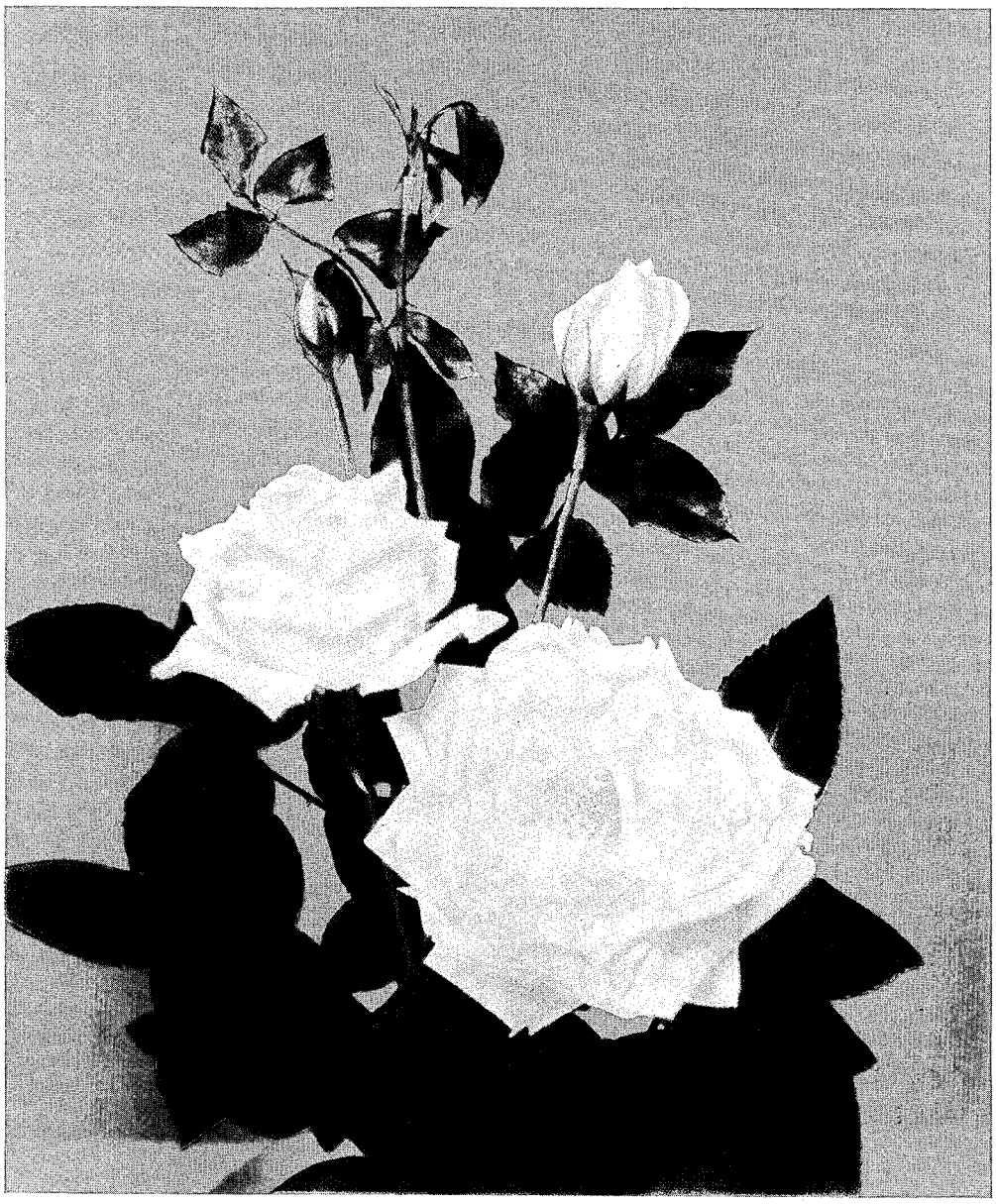
Inventor
C. Hartgerink
By Robb & Robb
Attorneys Patented Jan. 10, 1950

Plant Pat. 912

UNITED STATES PATENT OFFICE

912

ROSE PLANT

Conrad Hartgerink, West Los Angeles, Calif., assignor to Jackson & Perkins Company, Newark, N. Y., a corporation of New York Application October 27, 1948, Serial No. 56,815

1 Claim. (Cl. 47—61)

This discovery relates to a new and distinct variety of rose plant, originating as a sport of the variety "Starlite" (Pl. Pat. No. 414), and differing therefrom primarily in its smaller size bloom and more prolific production of these blooms.

This new rose further differs from its parent in that it produces a lesser number of petals and has a better opening characteristic.

Still further differences reside in the flat base form of the thorns, the Yellowish Oil Green color of the new foliage with edges and serrations of Oxblood Red, and the Cedar Green upper surface and Light Elm Green color of the under surface of the old foliage.

Asexual reproduction shows that these characteristics hold true through succeeding propagations.

In the accompanying drawings are illustrated, as nearly accurate as possible to reproduce, specimens of the new variety at different stages of development of the blooms from bud to full blown flowers, and on a reduced scale.

The following is a detailed description of the new variety, color terminology being in accordance with Ridgway's Color Standards and Nomenclature:

Parentage: Sport. *Parent variety*—"Starlite."
Classification: Hybrid tea.

*Flower*

Observations made in the month of May at Newark, New York.

Blooming habit: Recurrent—continuous.

Bud:

*Size.*—Medium.

*Form.*—Ovoid. Is not affected by wet or hot weather.

*Color.*—When sepals first divide—Glass Green, Plate 31. When petals begin to unfurl—Sea-Foam Yellow, Plate 31. When half blown—inside of petals—White, Plate 53, with a trace of Marguerite Yellow, Plate 30; reverse of petals—White, Plate 53, to Sea-Foam Yellow, Plate 31.

*Sepals.*—Branched. Curl back when petals begin to unfurl. Color—inside—Kildare Green, Plate 31; outside—Parrot Green, Plate 6.

*Calyx.*—Shape—funnel. Size—small. Aspect—smooth. Color—Biscay Green, Plate 17.

*Peduncle.*—Length—medium. Aspect—smooth. Color—Yellowish Oil Green, Plate 5. Strength—stiff; erect; heavy.

*Opening.*—Opens up well. Is not affected by adverse weather conditions.

Bloom:

*Size.*—Medium. Average size when fully expanded, 4½".

*Borne.*—Singly and several together.

*Stems.*—Medium length; strong.

*Form.*—When first open—high center. Permanence—retains its form to the end.

*Petalage.*—Very double (many petals and stamens hidden). Number of petals under normal conditions, 40.

*Color.*—Center of flower—White, Plate 53, overlaid with Marguerite Yellow, Plate 30. Outer petals—White, Plate 53. Base of petals (aiglet)—Pale Green Yellow, Plate 5. Inside of petals—White, Plate 53, with a slight tint of Pale Chalcedony Yellow, Plate 17, coming from the base of the petal. Reverse of petals—White, Plate 53, with a slight tint of Pale Chalcedony Yellow, Plate 17, coming from the base of the petal. General tonality from a distance—White, Plate 53.

*Discoloration.*—General tonality at end of first day—White, Plate 53. Second day—White, Plate 53. Third day—White, Plate 53.

Petals:

*Texture.*—Thin. Is not affected by wet or hot weather.

*Appearance.*—Inside and outside satiny.

*Form.*—Oval.

*Arrangement.*—Imbricated regularly arranged shingle-like). Petaloids in center—few; large.

*Persistence.*—Hang on and dry.

*Fragrance.*—Slight. Nature—tea.

*Lasting quality.*—On the plant—long; as cut flower—very long.

Genital organs:

*Stamens, anthers.*—Medium size; few. Color—Maize Yellow, Plate 4, very edge Capucine Orange, Plate 3. Arrangement—regular around styles.

*Stamens, filaments (threads).*—Medium length. Color—Pale Greenish Yellow, Plate 5.

*Pollen.*—Color—Baryta Yellow, Plate 4.

*Styles.*—Loosely separated, uneven length; medium long; thin.

*Stigmas.*—Color—Naphthaline Yellow, Plate 16.

*Ovaries.*—Some protruding from calyx.

*Plant*

Form: Bush.
Growth: Vigorous; upright.
Foliage: 5 to 7 leaflets.
*Size.*—Large.
*Quantity.*—Abundant.
*Color.*—New foliage: upper side—Yellowish Oil Green, Plate 5, edges and serrations Oxblood Red, Plate 1; under side—Hay's Russet, Plate 14. Old foliage: upper side—Cedar Green, Plate 6; under side—Light Elm Green, Plate 17.
*Shape.*—Oval pointed.
*Texture.*—Upper side—smooth; flat. Under side—smooth. Ribs and veins—prominent.
*Edge.*—Serrated (saw toothed).
*Serration.*—Single; small.
*Leaf stem.*—Color—Light Elm Green, Plate 17. Under side—smooth.
*Stipules.*—Long; smooth.
*Disease resistance.*—Resistant.
Wood:
*New wood.*—Color—Oil Green, Plate 5. Bark—smooth.

*Old wood.*—Color—Cress Green, Plate 31. Bark—smooth.
Thorns:
*Thorns.* — *Quantity* — on main stalks from base and on laterals from stalk—ordinary. Form—flat base; medium length; hooked downward. Color when young—Corinthian Red, Plate 27. Position—irregular.
*Prickles and hairs.*—None.

I claim:

A new and distinct variety of rose plant originating as a sport of "starlite," characterized as to novelty by the smaller size and greater prolificacy of production of the blooms than found in its parent variety; by the lesser number of petals and better opening characteristic of the blooms than said parent; and by the further differences in the form of the thorns and coloring of both the young and old foliage, substantially as shown and described.

CONRAD HARTGERINK.

No references cited.